(12) United States Patent
Linder et al.

(10) Patent No.: US 7,357,943 B2
(45) Date of Patent: *Apr. 15, 2008

(54) PHARMACEUTICAL PREPARATION IN THE FORM OF A SUSPENSION COMPRISING AN ACID-LABILE ACTIVE INGREDIENT

(75) Inventors: Rudolf Linder, Constance (DE); Rango Dietrich, Constance (DE)

(73) Assignee: Nycomed GmbH, Constance (DE)

( * ) Notice: Subject to any disclaimer, the term of this patent is extended or adjusted under 35 U.S.C. 154(b) by 539 days.

This patent is subject to a terminal disclaimer.

(21) Appl. No.: 10/433,305

(22) PCT Filed: Dec. 5, 2001

(86) PCT No.: PCT/EP01/14254

§ 371 (c)(1),
(2), (4) Date: Sep. 24, 2003

(87) PCT Pub. No.: WO02/45692

PCT Pub. Date: Jun. 13, 2002

(65) Prior Publication Data

US 2004/0052832 A1 Mar. 18, 2004

(30) Foreign Application Priority Data

Dec. 7, 2000 (EP) .................................. 00126829

(51) Int. Cl.
*A61K 9/14* (2006.01)
(52) U.S. Cl. ...................... 424/442; 424/484; 424/485; 424/486; 424/487
(58) Field of Classification Search ..................... None
See application file for complete search history.

(56) References Cited

U.S. PATENT DOCUMENTS

| | | | |
|---|---|---|---|
| 4,999,189 A | * | 3/1991 | Kogan et al. ................ 424/493 |
| 5,708,017 A | | 1/1998 | Dave et al. |
| 5,997,903 A | * | 12/1999 | Dietrich et al. ............. 424/482 |
| 6,569,453 B2 | | 5/2003 | Linder et al. |
| 2004/0058896 A1 | | 3/2004 | Dietrich et al. |
| 2004/0101558 A1 | | 5/2004 | Dietrich et al. |
| 2004/0110661 A1 | | 6/2004 | Dietrich et al. |
| 2006/0127477 A1 | | 6/2006 | Dietrich et al. |

FOREIGN PATENT DOCUMENTS

| | | |
|---|---|---|
| DE | 199 25 710 A1 | 12/2000 |
| EP | 0 005 129 B1 | 10/1979 |
| EP | 0 166 287 A1 | 1/1986 |
| EP | 0 174 726 B1 | 3/1986 |
| EP | 0 244 380 B1 | 11/1987 |
| EP | 0 268 956 B2 | 6/1988 |
| WO | 94/25070 | 11/1994 |
| WO | 00/50038 | 8/2000 |
| WO | 00/74654 A1 | 12/2000 |

OTHER PUBLICATIONS

Lewis et al. The physical and chemical stability of suspensions of sustained-release diclofenac microspheres. J Microencapsul. Sep.-Oct. 1998;15(5):555-67).*

L. Lewis, et al. "The physical and chemical stability of suspensions of sustained-release diclofenac microspheres." MICROENCAPSULATION. vol. 15, No. 5, pp. 555-567, 1998.

* cited by examiner

*Primary Examiner*—Michael G. Hartley
*Assistant Examiner*—Jake M. Vu
(74) *Attorney, Agent, or Firm*—The Nath Law Group; Joshua B. Goldberg; Sheldon M. McGee

(57) ABSTRACT

The present invention relates to the field of pharmaceutical technology and describes a novel pharmaceutical preparation in the form of a suspension comprising an acid-labile active ingredient, in particular an acid-labile proton pump inhibitor. The invention also relates to processes for producing the suspension. The suspension is particularly suitable for administering acid-labile active ingredients to people who have difficulty taking solid dosage forms such as tablets or capsules.

23 Claims, No Drawings

PHARMACEUTICAL PREPARATION IN THE FORM OF A SUSPENSION COMPRISING AN ACID-LABILE ACTIVE INGREDIENT

This application was filed under 35 U.S.C. 371 as a national stage of PCT/EP01/14254, filed Dec. 5, 2001.

TECHNICAL FIELD

The present invention relates to the field of pharmaceutical technology and describes a novel pharmaceutical preparation in the form of a suspension comprising an acid-labile active ingredient, in particular an acid-labile proton pump inhibitor. The invention also relates to processes for producing the suspension. The suspension is particularly suitable for administering acid-labile active ingredients to people who have difficulty taking solid dosage forms such as tablets or capsules.

BACKGROUND ART

It is generally known to coat oral dosage forms, e.g. tablets or pellets, which comprise an acid-labile active ingredient, with an enteric coating which, after passing through the stomach, rapidly dissolves in the alkaline medium in the intestine. One example of such acid-labile active ingredients comprises acid-labile proton pump inhibitors ($H^+/K^+$-ATPase inhibitors), in particular pyridin-2-ylmethylsulfinyl-1H-benzimidazoles like those disclosed, for example, in EP-A-0 005 129, EP-A-0 166 287, EP-A-0 174 726 and EP-A-0 268 956. Because of their $H^+/K^+$-ATPase-inhibiting effect, they are important in the therapy of disorders originating from increased gastric acid secretion. Examples of active ingredients from this group which are already commercially available are 5-methoxy-2-[(4-methoxy-3,5-dimethyl-2-pyridinyl)methylsulfinyl]-1H-benzimidazole (INN: omeprazole), 5-difluoromethoxy-2-[(3,4-dimethoxy-2-pyridinyl)methylsulfinyl]-1H-benzimidazole (INN: pantoprazole), 2-[3-methyl-4-(2,2,2-trifluoroethoxy)-2-pyridinyl)methylsulfinyl]-1H-benzimidazole (INN: lansoprazole) and 2-{[4-(3-methoxypropoxy)-3-methylpyridin-2-yl]methylsulfinyl}-1H-benzimidazole (INN: rabeprazole).

Because of their great tendency to decompose in a neutral and, in particular, acidic environment, with production also of highly colored decomposition products, it is also necessary in this case for oral preparations to protect active ingredients from the effect of acids. With the very acid-labile pyridin-2-ylmethylsulfinyl-1H-benzimidazoles it is additionally necessary for them to be processed in the tablet core or in pellets in the form of their alkaline salts, for example as sodium salts, or together with alkaline substances. Since substances suitable for enteric coatings are those with free carboxyl groups, the problem arises that the enteric coating is, because of the alkaline medium in the interior, partially or even completely dissolved from inside, and the free carboxyl groups promote decomposition of the active ingredient. It is therefore necessary to provide a sealing intermediate layer (subcoating) between the enteric coating and the alkaline tablet core or pellet. EP-A-0 244 380 proposes that cores which contain the active ingredient together with alkaline compounds or as alkaline salt be coated with at least one layer which is soluble in water or rapidly disintegrates in water and is composed of nonacidic, inert pharmaceutically acceptable substances, before the enteric layer is applied. The intermediate layer or intermediate layers act as pH-buffering zones in which hydrogen ions diffusing in from outside are able to react with the hydroxyl ions diffusing out of the alkaline core. In order to increase the buffer capacity of the intermediate layer, it is proposed to incorporate buffer substances into the intermediate layer(s). By this process it is possible in practice to obtain reasonably stable preparations. However, relatively thick intermediate layers are required in order to avoid the unsightly discolorations which occur even with only slight decomposition. In addition, considerable effort must be invested to avoid traces of moisture during production.

The administration of solid dosage forms such as capsules or tablets proves to be problematic especially in animals or patients who have difficulties with swallowing, such as, for example, elderly people and small children.

WO94/25070 describes an oral pharmaceutical preparation comprising a proton pump inhibitor in the form of a paste for treating acid-related gastric disorders in animals. For this purpose, enteric coated particles (such as tablets or beads) which comprise a proton pump inhibitor either are mixed with dry gelling agents, and this mixture is then mixed with water immediately before administration, or the enteric particles are mixed with potassium or calcium salts and mixed immediately before administration with a low-viscosity solution of a polymeric gel-forming agent. An alternative proposal is to mix enteric coated particles immediately before administration with a low-viscosity solution of a gel-forming agent in the form of a temperature-sensitive polymer, and to heat the solution cautiously. The preparations described herein have the disadvantage for the user, however, that the paste must be prepared immediately before administration.

U.S. Pat. No. 5,708,017 and WO00/50038 describe an oral pharmaceutical preparation which is ready for use and comprises omeprazole in the form of a paste for treating acid-related gastric disorders in humans and animals. This preparation in paste form comprises omeprazole, basifying agents, a thickener and a hydrophobic, oily liquid vehicle. The hydrophobic oily liquid vehicle comprises a vegetable oil and triglycerides of medium chain length fatty acids or propylene glycol diesters of medium chain length fatty acids. According to WO00/50038, these preparations are stable and can be used to fill syringes which can then be used directly for administering the active ingredient to an animal.

DESCRIPTION OF THE INVENTION

It is an object of the present invention to provide a juice (hereinafter also referred to as suspension) for the oral administration of acid-labile active ingredients which can be produced without great technical complexity, which is stable and not sensitive to moisture and displays good controllability of active ingredient delivery. It ought also to be possible to produce the suspension ready for use. Another object of the invention is also to provide a suspension for the oral administration of acid-labile active ingredients, where it is unnecessary to protect the acid-labile active ingredient by an enteric coating.

It has now been found, surprisingly, that this object can be achieved by a pharmaceutical preparation where a plurality of individual active ingredient units are dispersed in a thickened base composed of one or more pharmaceutical excipients, where the acid-labile active ingredient is present in the individual active ingredient units in a matrix composed of a mixture comprising at least one solid paraffin and one or more substances from the group of fatty alcohol, triglyceride and fatty acid ester.

The invention therefore relates to a pharmaceutical preparation in juice (suspension) form for oral administration of an acid-labile active ingredient where a plurality of individual active ingredient units are dispersed in a thickened base composed of one or more pharmaceutical excipients, where the acid-labile active ingredient is present in the individual active ingredient units in a matrix composed of a mixture comprising at least one solid paraffin and one or more substances from the group of fatty alcohol, triglyceride and fatty acid ester.

The invention therefore further relates to a pharmaceutical preparation in suspension form for oral administration of an acid-labile active ingredient where a plurality of individual active ingredient units are dispersed in a thickened base composed of one or more pharmaceutical excipients, where the acid-labile active ingredient is present in the individual active ingredient units i) in a matrix composed of a mixture comprising at least one fatty alcohol and at least one solid paraffin, ii) in a matrix composed of a mixture comprising at least one triglyceride and at least one solid paraffin or iii) in a matrix composed of a mixture comprising at least one fatty acid ester and at least one solid paraffin.

The dosage form can according to the invention be in the form of a powder for reconstitution, that is to say the ingredients are in the form of a dry mixture. The powder for reconstitution is mixed with water immediately before use and must then be consumed within a specified period. The dosage form of the invention is preferably a suspension ready for use.

The pharmaceutical preparation of the invention can be produced without great technical complexity. Technically complicated processes for applying enteric layers and intermediate layers are unnecessary. In addition, the controllability of active ingredient deliveries from the suspension is observed to be good. Surprisingly, this suspension ready for use is also observed to have good chemical and physical stability.

Further subject matters are evident from the claims.

The numerous individual active ingredient units (also referred to hereinafter as preparations) for the purposes of the invention comprise numerous individual units in which at least one active ingredient particle, preferably a plurality of active ingredient particles, is present in a matrix composed of a mixture comprising at least one solid paraffin and one or more substances from the group of fatty alcohol, triglyceride and fatty acid ester. A plurality of active ingredient particles is preferably present i) in a matrix composed of a mixture comprising at least one fatty alcohol and at least one solid paraffin, ii) in a matrix composed of a mixture of at least one triglyceride and at least one solid paraffin or iii) in a matrix composed of a mixture of at least one fatty acid ester and at least one solid paraffin. The active ingredient is preferably present in essentially uniform distribution, in particular homogeneously dispersed or dissolved, in the matrix. The active ingredient units are preferably microspheres.

The active ingredient units of the invention are distinguished in particular by high stability, an active ingredient release which can be controlled via the particle size and composition of the matrix, good flow characteristics, good processibility and a uniform delivery of active ingredient. It is particularly worthy of mention that the active ingredient units of the invention can be further processed to the suspension without thereby losing a given functionality (such as taste masking, resistance to gastric juice, slowing of release) in the suspension base.

The particle size of the individual units is advantageously less than or equal to 2 mm, preferably 50-800 µm, particularly preferably 50-700 µm and very particularly preferably 50-600 µm. Microspheres with a particle size of 50-500 µm, particularly preferably of 50-400 µm, are preferred. Monomodal microspheres with a particle size of 50-400 µm, particularly preferably of 50-200 µm, are particularly preferred.

Examples of acid-labile active ingredients in the sense of the present invention are acid-labile proton pump inhibitors.

Acid-labile proton pump inhibitors ($H^+/K^+$-APTase inhibitors) in the sense of the present invention which should be particularly mentioned are substituted pyridin-2-ylmethylsulfinyl-1H-benzimidazoles like those disclosed, for example, in EP-A-0 005 129, EP-A-0 166 287, EP-A-0 174 726, EP-A-0 184 322, EP-A-0 261 478 and EP-A-0 268 956. Those which may be mentioned as preferred in this connection are 5-methoxy-2-[(4-methoxy-3,5-dimethyl-2-pyridinyl)methylsulfinyl)-1H-benzimidazole (INN: omeprazole), 5-difluoromethoxy-2-[(3,4-dimethoxy-2-pyridinyl) methylsulfinyl]-1H-benzimidazole (INN: pantoprazole), 2-[3-methyl-4-(2,2,2-trifluoroethoxy)-2-pyridinyl)methyl-sulfinyl)-1H-benzimidazole (INN: lansoprazole) and 2-{[4-(3-methoxypropoxy)-3-methylpyridin-2-yl]methylsulfinyl)-1H-benzimidazole (INN: rabeprazole).

Further acid-labil proton pump inhibitors, for example substituted phenylmethylsulfinyl-1H-benzimidazoles, cycloheptapyridin-9-ylsulfinyl-1H-benzimidazoles or pyridin-2-ylmethylsulfinylthienoimidazoles are disclosed in DE-A 35 31 487, EP-A-0 434 999 and EP-A-0 234 485. Examples which may be mentioned ar 2-[2-(N-isobutyl-N-methylamino)benzylsulfinyl]benzimidazole (INN: leminoprazole) and 2-(4-methoxy-6,7,8,9-tetrahydro-5H-cyclohepta[b]pyridin-9-ylsulfinyl)-1H-benzimidazol (INN: nepaprazole).

The acid-labile proton pump inhibitors are chiral compounds. The term "acid-labile proton pump inhibitor" also encompasses the pure enantiomers of the acid-labile proton pump inhibitors and their mixtures in any mixing ratio. Pure enantiomers which may be mentioned by way of example are 5-methoxy-2-[(S)-[(4-methoxy-3,5-dimethyl-2-pyridinyl)methyl]sulfinyl]-1H-benzimidazole (INN: esomeprazole) and (S)-pantoprazole[(−)-pantoprazole].

The acid-labile proton pump inhibitors are moreover present as such or, preferably, in the form of their salts with bases. Examples of salts with bases which may be mentioned are sodium, potassium, magnesium or calcium salts. If the acid-labile proton pump inhibitors are isolated in crystalline form, they may contain variable amounts of solvent. The term acid-labile proton pump inhibitor therefore also represents according to the invention all soivates, in particular all hydrates, of the acid-labile proton pump inhibitors and their salts. Such a hydrate of the salt of an acid-labile proton pump inhibitor with a base is disclosed, for example, in WO91/19710.

Acid-labile proton pump inhibitors which may be mentioned as particularly preferred are pantoprazole sodium sesquihydrate (=pantoprazole sodium×1.5 $H_2O$), (−)-pantoprazole sodium sesquihydrate, Pantoprazole magnesium dihydrate, omeprazole magnesium, omeprazole and esomeprazole.

The fatty alcohol is preferably a linear, saturated or unsaturated primary alcohol with 10-30 carbon atoms. It is preferably a primary alcohol with 10 to 18 carbon atoms in linear chains. Examples of fatty alcohols which may be mentioned are cetyl alcohol, myristyl alcohol, lauryl alcohol or stearyl alcohol, with preference for cetyl alcohol. It is also possible if desired for mixtures of fatty alcohols to be present.

The triglyceride is glycerol with its three hydroxyl groups esterified by carboxylic acids. The carboxylic acids are preferably monobasic carboxylic acids with 8 to 22 carbon atoms, preferably naturally occurring carboxylic acids. It is possible in this case for the carboxylic acids to be different or, preferably, identical. Examples which may be mentioned are tristearate, tripalmitate and, particularly preferably, trimyristate (these triglycerides are commercially available under the name Dynasan 118, 116 and 114 respectively). It is also possible if desired for mixtures of triglycerides to be present.

The fatty acid ester is the ester of an alcohol with a fatty acid. The alcohol in this case is preferably a linear, saturated or unsaturated primary alcohol with 10-30, preferably with 12 to 18,carbon atoms. The fatty acid is preferably a monobasic carboxylic acid with 8 to 22, in particular 12 to 18, carbon atoms, preferably a naturally occurring carboxylic acid. Fatty acid esters preferred according to the invention have a melting point above 30° C. Examples of fatty acid esters which may be mentioned are cetyl palmitate, which is commercially available for example under the name Cutina® CP. It is also possible if desired for mixtures of fatty acid esters to be present.

The solid paraffin is preferably paraffinum solidum (ceresin). It is also possible alternatively to use ozokerite, for example. It is also possible if desired to use mixtures.

If desired, the mixtures in the individual active ingredient units may include one or more other pharmaceutically suitable excipients. Other suitable excipients which may be mentioned by way of example are polymers, sterols and basic compounds.

Examples of polymers which may be mentioned are povidone (e.g. Kollidon® 17, 30 and 90 from BASF), vinylpyrrolidone/vinyl acetate copolymer and polyvinyl acetate. Others which may be mentioned are cellulose ethers [such as, for example, methylcellulose, ethylcellulose (Ethocel®) and hydroxypropylmethylcellulose], cellulose esters [such as cellulose acetate phthalate (CAP), cellulose acetate trimellitate (CAT), hydroxypropylmethylcellulose phthalate (HP50 and HP55) or hydroxypropylmethylcellulose acetate succinate (HPMCAS)], methacrylic acid/methyl methacrylate copolymer or methacrylic acid/ethyl methacrylate copolymer (Eudragit® L). The polymer is preferably povidone or ethylcellulose. It is also possible if desired for mixtures of polymers to be present. It is possible by adding suitable polymers, for example, to influence the pharmaceutical properties of the individual active ingredient units (e.g. delivery of the active ingredient).

The sterol is preferably a phytosterol or a zoosterol. Examples of phytosterols which may be mentioned are ergosterol, stigmasterol, sitosterol, brassicasterol and campesterol. Examples of zoosterols which may be mentioned are cholesterol and lanosterol. It is also possible if desired for mixtures of sterols to be present.

Examples of suitable basic compounds are inorganic basic salts such as ammonium carbonate and sodium carbonate, salts of fatty acids such as sodium stearate, amines such as meglumine, di-, triethylamine and TRIS(2-amino-2-hydroxymethyl-1,3-propanediol) or fatty-amines such as stearylamine. Stearylamine and sodium stearate may be mentioned as preferred. The addition of basic compounds to the mixtures in the individual units results in particularly stable preparations and prevents possible discolorations.

The proportion (in percent by weight) of active ingredient in the individual active ingredient unit is advantageously 1-90%. The proportion of active ingredient is preferably 2-70%, particularly preferably 5-40%, in particular 10-20%.

The proportion of fatty alcohol in the individual active ingredient unit is advantageously 10-70%, preferably 20-70%, particularly preferably 20-60% and in particular 30-60%.

The proportion of triglyceride in the individual active ingredient unit is advantageously 10-70%, preferably 20-70%, particularly preferably 20-60% and in particular 30-60%. The proportion of fatty acid ester in the individual active ingredient unit is advantageously 10-70%, preferably 20-70%, particularly preferably 20-60% and in particular 30-60%. The proportion of solid paraffin is advantageously 10-70%, preferably 20-60% and in particular 30-60%. If present, the proportion of polymer in the individual active ingredient unit is expediently 1-25%, preferably 1-10%, particularly preferably 5-10%. If present, the proportion of sterol is expediently 1-10%, preferably 1-5%. If present, the proportion of basic compound is 0.05-5%, preferably 0.1-1%.

Preferred individual active ingredient units of the invention consist of 2-70% active ingredient, 10-60% fatty alcohol, 10-60% solid paraffin, 1-15% polymer and 0.1-2% of a basic compound. Further preferred individual active ingredient units of the invention consist of 2-70% active ingredient, 10-60% triglyceride, 10-60% solid paraffin, 1-15% polymer and 0.1-2% of a basic compound. Other preferred individual active ingredient units of the invention consist of 2-70% active ingredient, 10-60% fatty acid ester, 10-60% solid paraffin, 1-15% polymer and 0.1-2% of a basic compound.

Particularly preferred individual active ingredient units of the invention consist of 5-40% active ingredient, 20-60% fatty alcohol, 10-60% solid paraffin, 1-15% polymer and 0.1-1% of a basic compound. Further particularly preferred individual active ingredient units of the invention consist of 5-40% active ingredient, 20-60% triglyceride, 10-60% solid paraffin, 1-15% polymer and 0.1-1% of a basic compound. Other particularly preferred individual active ingredient units of the invention consist of 5-40% active ingredient, 20-60% fatty acid ester, 10-60% solid paraffin, 1-15% polymer and 0.1-1% of a basic compound.

Examples of active ingredient units of the invention contain 5-40% pantoprazole sodium sesquihydrate, 10-40% cetyl alcohol, 5-60% solid paraffin, 1-5% polymer and 0.1-0.2% of a basic compound. Further examples of active ingredient units of the invention contain 5-40% pantoprazole sodium sesquihydrate, 10-40% glyceryl tripalmitate, 5-60% solid paraffin, 1-5% polymer and 0.1-0.2% of a basic compound. Other examples of active ingredient units of the invention contain 5-40% pantoprazole sodium sesquihydrate, 10-40% glyceryl tripalmitate, 5-60% solid paraffin, 1-5% polymer and 0.1-0.2% of a basic compound. Still other examples of active ingredient units of the invention contain 10-20% pantoprazole sodium sesquihydrate, 20-40% triglyceride, 40-70% solid paraffin, 1-5% sterol and 0.05-0.1% of a basic compound.

The individual active ingredient units can be produced for example by spray drying or, preferably, by spray solidification, in particular also by spray prilling. Production is particularly preferably by prilling, in particular by vibration prilling.

For the spray solidification or prilling expediently the fatty alcohol, the triglyceride or the fatty acid ester is liquefied together with the solid paraffin and, if desired, other excipients to give a clear melt. The active ingredient is dissolved or dispersed in this solution, and the resulting solution or dispersion is sprayed or, preferably, prilled in a suitable apparatus. A dispersion of the active ingredient in a melt of the excipients is preferably used.

Spray solidification takes place in a manner known per se. A detailed description of this technique is to be found in P.B. Deasy, Microencapsulation and Related Drug Processes (1984).

The individual active ingredient units are particularly preferably produced by solidification from liquid phase by generating drops by means of vibrating nozzles and by solidifying the drops which are formed, after they have stabilized, by drying or cooling in a suitable medium (preferably gaseous or liquid). The suitable medium may be, for example, cooled gas such as air or nitrogen. Processes of this type and corresponding apparatuses are disclosed in DE 27 25 924, EP 0 467 221, WO99/33555 and WO00/24382. It is particularly preferred in this connection for the liquid phase flowing to the nozzle to be kept at a constant temperature. The solidification preferably takes place by instantaneous cooling in a suitable cooling medium. In prilling, moreover it is preferred for the liquid phase flowing to the nozzle, the vibrating nozzle and the drops formed by prilling to be kept at a constant temperature until their spherical shape has stabilized, and for the solidification of the drops after their stabilization to be carried out instantaneously by cooling with a gaseous or liquid cooling medium. Systems suitable for prilling by means of vibrating nozzles are marketed, for example, by Brace GmbH, Alzenau, Germany. It is possible by means of prilling using vibrating nozzles to obtain the individual active ingredient units in the form of microspheres with a narrow monomodal particle size spectrum in the particle size range from 50 μm to 2 mm. The narrow monomodal particle size spectrum and the uniform spherical shape of the microspheres obtained in this way are expected to result in a uniformly smooth surface, a uniform, defined delivery of active ingredient and, in relation to passage through the stomach in the case of oral dosage forms (owing to the small particles), a behavior like that of a solution. The microspheres of the invention are distinguished in particular by high stability, a release of active ingredient which can be controlled via the particle size and composition of the matrix, good flow characteristics, good processibility and a uniform delivery of active ingredient. It is particularly worthy of mention that the microspheres can be-further processed-to the-suspension without thereby losing a given functionality (such as taste masking, resistance to gastric juice, slowing of release) in the thickened base.

The microspheres are preferably monomodal microspheres with a particle size range of 50-800 μm, preferably 50-500 μm, particularly preferably 50-400 μm, in particular 50-200 μm. The microspheres preferably comprise an acid-labile proton pump inhibitor.

The particle size of the active ingredient employed in the spray drying or spray solidification, prilling or vibration prilling is advantageously less than or equal to 100 μm, in particular less than 40 μm. The particle size is preferably in the range 1-20 μm, particularly preferably in the range 3-15 μm. Such a particle size can be achieved, for example, by grinding the active ingredient in a suitable mill.

The individual active ingredient units (preparations) of the invention can then be further processed together with suitable excipients to give the suspension of the invention—in the form of a powder for reconstitution or ready for use. Suitable excipients are, in particular, those excipients normally used to produce suspensions. Excipients particularly suitable according to the invention are those with which a thickened base can be produced, such as thickeners. Examples of thickeners according to the invention are xanthan, substituted celluloses, polyvinylpyrrolidone (polyvidone types), sheet silicates, alginates or alginic acids. A mixture of two or more different thickeners is also possible if desired. The proportion of thickener depends on the desired viscosity or consistency which the suspension ready for use is to have. A particularly preferred suspension has a viscosity of less than 500 mPa.s (determined with a rotational viscometer). The proportion of xanthan based on the suspension ready for use is usually from 0.1 to 1% by weight. The proportion of substituted celluloses depends on the viscosity levels of the celluloses and is normally from 0.1 to 10% by weight based on the suspension ready for use. Examples of substituted celluloses of the invention which may be mentioned are carboxymethylcellulose, ethylcellulose, methylcellulose or hydroxypropylcellulose. The proportion of polyvinylpyrrolidone (polyvidone types) is normally from 0.1 to 10% by weight based on the solution ready for use. Sheet silicates such as Veegum or bentonites can be employed alone or in combination with water-soluble thickeners. The total proportion of thickener is then advantageously from 0.1 to 7% by weight based on the suspension ready for use. Alginates and alginic acid are normally employed in a proportion of from 0.1 to 10% by weight based on the suspension ready for use. Other pharmaceutical excipients preferably employed are insoluble crosslinked polyvinylpyrrolidone (crospovidone) and microcrystalline cellulose. It is observed in this case that a loose sediment forms and prevents agglomeration of individual active ingredient units. The ratio of crospovidone to the individual active ingredient units is advantageously from 1:1 to 0.5:1 (based on weight). Microcrystalline cellulose, which is normally employed in a proportion of from 0.5 to 5% by weight based on the suspension ready for use, is likewise suitable for this purpose. The proportion of individual active ingredient units in the suspension ready for use is usually according to the invention from 1 to 20% by weight based on the suspension ready for use, preferably from 1 to 15% by weight and very preferably from 5 to 10% by weight. Water is preferably used as solvent or dispersant for the suspension Other suitable excipients which may be present in the suspension of the invention are, for example, flavoring substances (such as flavorings and sweeteners), buffer substances, preservatives or else emulsifiers. Flavors are usually added in a proportion of from 0.05 to 1% by weight. Other examples of flavoring substances are acids such as citric acid, sweeteners such as saccharin, aspartame, cyclamate sodium or maltol, which are added according to the desired result. Examples of emulsifiers are lecithins, sodium lauryl sulfate, Tweens® or Spans, which are normally added in a proportion of from 0.01 to 1% by weight. Preservatives such as benzoic acid, salts of benzoic acid, methyl 4-hydroxybenzoate, propyl 4-hydroxybenzoate, sorbic acid or salts thereof are preferably also added. The proportion depends on the preservative used and is usually from 0.1 to 4% by weight based on the suspension ready for use.

The suspension of the invention is produced by techniques known to the skilled worker. If a powder for reconstitution is to be produced, there is preferably production of a mixture of the individual active ingredient units with the thickener and, where appropriate, other excipients. This mixed powder for reconstitution is then mixed with a suitable amount of water immediately before administration. Suspension ready for use is normally produced by introducing the individual active ingredient units into a dispersion of the thickener and, where appropriate, of additives in water or, alternatively, by introducing the thickener into a dispersion of the individual active ingredient units in water.

The pharmaceutical preparations of the invention in suspension form are administered in amounts which contain the acid-labile active ingredient in the dose usual for treating the particular disorder. The acid-labile proton pump inhibitors of the invention can be used for the treatment and prevention of all disorders regarded as treatable or preventible by use of pyridin-2-ylmethylsulfinyl-1H-benzimidazoles. In particular, the suspension of the invention can be employed in the treatment of gastric disorders. As mentioned above, the suspension of the invention is particularly suitable for oral administration of the active ingredient to humans who have difficulties with swallowing solid oral forms, such as elderly people or else children. For administration to humans, the suspension of the invention is provided in amounts which contain between 1 and 500 mg, preferably between 5 and 60 mg, of an acid-labile proton pump inhibitor. Examples which may be mentioned are units of the suspensions of the invention which contain 10, 20, 40 or 50 mg of pantoprazole. Administration of the daily dose (for example 40 mg of active ingredient) can take place for example in the form of a single dose or by means of several doses of the suspension of the invention (for example 2×20 mg of active ingredient). The total volume of suspension for an administration unit is advantageously from 1 to 10 ml. The suspension of the invention is preferably provided in a special pack which may also at the same time assist administration. Examples which may be mentioned are bags or bottles. Compared with solid oral forms, the suspension of the invention has the advantage for the patient that it can be taken very simply and anywhere because, in the case of the suspension ready for use, intake is possible even without water, for example directly from a bag or bottle. The suspension additionally permits individual dosage.

The suspension of the invention can be combined with other medicaments, either in different combinations or in a fixed combination. Combinations worthy of mention in connection with the dosage forms of the invention which comprise acid-labile proton pump inhibitors as active ingredients are those with anti-microbial active ingredients and combinations with NSAIDs (nonsteroidal anti-inflammatory drugs). Particular mention should be made of the combination with antimicrobial agents like those employed for controlling the microbe *Helicobacter pylori* (*H. pylori*).

Examples of suitable antimicrobial active ingredients (active against *Helicobacter pylori*) are described in EP-A-0 282 131.Examples of antimicrobial agents which are suitable for controlling the microbe *Helicobacter pylori* and may be mentioned by way of example are bismuth salts [e.g. bismuth subcitrate, bismuth subsalicylate, ammonium bismuth(III) potassium citrate dihydroxide, bismuth nitrate oxide, dibismuth tris(tetraoxodialuminate)], but especially β-lactam antibiotics, for example penicillins (such as benzylpenicillin, phenoxymethylpenicillin, propicillin, azidocillin, dicloxacillin, flucloxacillin, oxacillin, amoxicillin, bacampicillin, ampicillin, meziocillin, piperacillin or azlocillin), cephalosporins (such as cefadroxil, cefaclor, cefalexin, cefixime, cefuroxime, cefetamet, ceftibuten, cefpodoxime, cefotetan, cefazoline, cefoperazone, ceftizoxime, cefotaxime, ceftazidime, cefamandole, cefepime, cefoxitin, cefodizime, cefsulodin, ceftriaxone, cefotiam or cefmenoxime) or other β-lactam antibiotics (e.g. aztreonam, loracarbef or meropenem); enzyme inhibitors, for example sulbactam; tetracyclines, for example tetracycline, oxytetracycline, minocycline or doxycycline; aminoglycosides, for example tobramycin, gentamicin, neomycin, streptomycin, amikacin, netilmicin, paromomycin or spectinomycin; amphenicols, for example chloramphenicol or thiamphenicol; lincomycins and macrolide antibiotics, for example clindamycin, lincomycin, erythromycin, clarithromycin, spiramycin, roxithromycin or azithromycin; polypeptide antibiotics, for example colistin, polymixin B, telcoplanin or vancomycin; gyrase inhibitors, for example norfiloxacin, cinoxacin, ciprofloxacin, pipemidic acid, enoxacin, nalidixic acid, pefloxacin, fieroxacin or ofloxacin; nitrolmidazoles, for example metronidazole; or other antibiotics, for example fosfomycin or fusidic acid. Particularly worthy of mention in this connection is the administration of an acid-labile proton pump inhibitor together with the combination of a plurality of antimicrobial active ingredients, for example with the combination of a bismuth salt and/or tetracycline with metronidazole or the combination of amoxicillin or clarithromycin with metronidazole and amoxicillin with clarithromycin.

The production of dosage forms and preparations of the invention is described by way of example hereinafter. The following examples explain the invention in detail without restricting it.

EXAMPLES

Production of the Active Ingredient Units

Example 1

50 g of solid paraffin, 34.9 g of cetyl alcohol and 0.1 g of stearylamine are converted into a clear melt. 5.0 g of povidone is dissolved in the clear melt. At a temperature between 56-60° C., 10.0 g of pantoprazole sodium sesquihydrate is added and suspended homogeneously. The suspension is prilled in the molten state, and the drops thus produced are solidified in a cooling zone.

Example 2

55 g of solid paraffin, 30.9 g of cetyl alcohol and 0.1 g of stearylamine are converted into a clear melt. 4.0 g of povidone is dissolved in the clear melt. At a temperature between 56-60° C., 10.0 g of pantoprazole magnesium is added and suspended homogeneously. The suspension is prilled in the molten state, and the drops thus produced are solidified in a cooling zone.

Example 3

45.0 g of solid paraffin, 33.8 g of cetyl alcohol, 1.0 g of β-sitosterol and 0.2 g of stearylamine are converted into a clear melt. 1.0 g of povidone and 4.0 g of ethylcellulose are dissolved in the clear melt. At a temperature between 56-60° C., 15.0 g of pantoprazole sodium sesquihydrate is added and suspended homogeneously. The suspension is prilled in the molten state, and the drops thus produced are solidified in a cooling zone.

Example 4

52.0 g of solid paraffin, 30.3 g of cetyl alcohol and 0.2 g of stearylamine are converted into a clear melt. 5.0 g of povidone is dissolved in the clear melt. At a temperature between 56-60° C., 12.5 g of pantoprazole sodium sesquihydrate is added and suspended homogeneously. The suspension is prilled in the molten state, and the drops thus produced are solidified in a cooling zone.

Example 5

77.2 g of cetyl alcohol and 0.3 g of stearylamine are converted into a clear melt. 10.0 g of povidone is dissolved in the clear melt. At a temperature between 56-60° C., 12.5 g of pantoprazole sodium sesquihydrate is added and suspended homogeneously. The suspension is prilled in the molten state, and the drops thus produc d are solidified in a cooling zone.

Example 6

47 g of solid paraffin, 40 g of glyceryl tripalmitate (Dynasan 116,from Hüls) and 3 g of sitosterol are converted into a clear melt at 100° C. and cooled to 55-60° C. 10 g of lansoprazole are added and suspended homogeneously. The suspension is put in the feed container of a prilling unit (from Brace) and prilled from a 200 µm nozzle at about 0.1 bar. A periodic vibration with a frequency of about 390 Hz is transmitted to the nozzle head during this. The resulting drops are solidified in a cooling zone with air at a temperature of −30° C.

Example 7

15 g of glyceryl trimyristate (Dynasan 114), 15 grams of glyceryl tripalmitate (Dynasan 116), 50 grams of solid paraffin and 5 g of cholesterol are converted into a clear melt at about 100° C. The clear melt is cooled to about 55-65° C. 15 g of rabeprazole are added, the active ingredient is uniformly dispersed, and the homogeneous suspension is prilled as in example 6.

Example 8

10 g of glyceryl tripalmitate (Dynasan 116), 20 g of glyceryl trimyristate (Dynasan 114), 52 g of solid paraffin and 3 g of sitosterol are converted into a clear melt at about 100° C. The clear melt is cooled to 55-65° C. 15 g of omeprazole Mg are added and suspended homogeneously. The suspension is put in the feed container of a prilling unit (from Brace) and prilled through a 200 µm nozzle at 90 mbar. A periodic vibration with a frequency of about 400 Hz is transmitted to the nozzle head during this. The resulting drops are solidified with air at a temperature of −30° C. in a cooling zone.

Example 9

18 g of tristearin, 60 g of solid paraffin and 5 g of cholesterol are converted into a clear melt. The clear melt is cooled to 56-60° C. 10 g of pantoprazole sodium sesquihydrate are introduced and homogeneously dispersed. The suspension is prilled in the molten state in a prilling unit (from Brace) with vibrating nozzles, and the resulting drops are solidified in a cooling zone.

Example 10

18 g of cetyl palmitate, 40 g of solid paraffin and 2 g of cholesterol are converted into a clear melt. The clear melt is cooled to 56-60° C. 10 g of pantoprazole sodium sesquihydrate are introduced and homogenized until a uniform suspension results. The suspension is prilled in the molten state in a prilling unit (from Brace) with vibrating nozzles, and the resulting drops are solidified in a cooling zone.

Example 11

50 g of solid paraffin and 40 g of cetyl palmitate (Cutina® CP) are converted into a clear melt at 100° C. The clear melt is cooled to 50-60° C. 10 g of pantoprazole sodium sesquihydrate are introduced and suspended homogeneously. The suspension is prilled in the molten state in a prilling unit (from Brace) with vibrating nozzles (200 µm nozzle), and the resulting drops are solidified in a cooling zone.

Example 12

50 g of solid paraffin and 40 g of cetyl alcohol are converted into a clear melt at 100° C. The clear melt is cooled to 50-60° C. 10 g of pantoprazole sodium sesquihydrate are introduced and suspended homogeneously. The suspension is prilled in the molten state in a prilling unit (from Brace) with vibrating nozzles (200 µm nozzle), and the resulting drops are solidified in a cooling zone.

Example 13

50 g of solid paraffin and 40 g of glyceryl trimyristate are converted into a clear melt at 100° C. The clear melt is cooled to 50-60° C. 10 g of pantoprazole sodium sesquihydrate are introduced and suspended homogeneously. The suspension is prilled in the molten state in a prilling unit (from Brace) with vibrating nozzles (200 µm nozzle), and the resulting drops are solidified in a cooling zone.

Example 14

47 g of solid paraffin, 40 g of glyceryl tripalmitate (Dynasan 116,from Hüls) and 3 g of sitosterol are converted into a clear melt at 100° C. and cooled to 50-60° C. 10 g of lansoprazole are added and suspended homogeneously. The suspension is put into the feed container of a prilling unit (from Brace) and prilled from a 200 µm nozzle at about 0.1 bar. A periodic vibration with a frequency of about 390 Hz is transmitted to the nozzle head during this. The resulting drops are solidified in a cooling zone with air at a temperature of −30° C.

Example 15

30 g of tristearin, 60 g of solid paraffin and 4 g of sitosterol and 0.07 g stearylamine are converted into a clear melt. The clear melt is cooled to 56-60° C. 15 g of pantoprazole sodium sesquihydrate are introduced and homogeneously dispersed. The suspension is prilled in the molten state in a prilling unit (from Brace) with vibrating nozzles, and the resulting drops are solidified in a cooling zone.

Example 16

17.59 of glyceryl trimyristate (Dynasan 114), 67.5 g of solid paraffin and 5 g of cholesterol are converted into a clear melt at about 100° C. The clear melt is cooled to about 55-65° C. 10 g of pantoprazole are added, and the active ingredient is uniformly dispersed, and the homogeneous suspension is prilled as in example 6.

Example 17

56.7 g of cetyl alcohol, 3 g of vinylpyrollidone/vinyl acetate copolymer, 15 g of solid paraffin, 15 g of cetyl palmitate and 0.1 g of sodium stearate are converted into a clear melt. At a temperature between 56-60° C., 10.0 g of pantoprazole sodium sesquihydrate is added and suspended homogeneously. The suspension is prilled in the molten state at 60° C. and the drops thus produced are solidified in a cooling zone.

Example 18

46.7 g of cetostearylic alcohol, 4 g of vinylpyrollidone/vinyl acetate copolymer, 23 g solid paraffin, 0.3 g of sodium stearate and 1 g sitosterol are converted into a clear melt. At a temperature between 60-65° C., 10.0 g of pantoprazole sodium sesquihydrate is added and suspended homogeneously. The suspension is prilled in the molten state at 60 to 65° C. and the drops thus produced are solidified in a cooling zone.

Example 19

39.9 g of cetyl alcohol, 3 g of vinylpyrollidone/vinyl acetate copolymer, 20 g of cetyl palmitate, 2 g cholesterol, 17 g solid paraffin and 0.1 g of sodium stearate are converted into a clear melt. At a temperature between 56-60° C., 18.0 g of pantoprazole sodium sesquihydrate is added and suspended homogeneously. The suspension is prilled in the molten state at 60° C. and the drops thus produced are solidified in a cooling zone.

Example 20

47.9 g cetostearylic alcohol, 2 g of vinylpyrollidone/vinyl acetate copolymer, 25 g of cetyl palmitate, 1 g sitosterol, 15 g solid paraffin and 0.1 g of sodium stearate are converted into a clear melt. At a temperature between 56-60° C., 15.0 g of pantoprazole sodium sesquihydrate is added and suspended homogeneously. The suspension is prilled in the molten state at 60° C. and the drops thus produced are solidified in a cooling zone.

The preparations obtained as in examples 1-20 have a particle size in the range 50-700 μm. It is possible, for example by varying the process conditions, to obtain larger particles.

Production of Solutions of the Invention

Example A 0.1 g of cyclamate sodium and 0.1 g of sodium benzoate are successively added to and dissolved in 100 ml of purified water. 4.0 g of a preparation obtained as in Example 1 are then stirred into the solution obtained in this way. 0.2 g of xanthan is added, and the mixture is stirred until uniform swelling is achieved. Flavors are also added if desired.

Example B 0.1 g of cyclamate sodium and 0.15 g of sodium benzoate are successively added to and dissolved in 100 ml of purified water. 4.0 g of a preparation obtained as in Example 8 are then stirred into the solution obtained in this way. 0.2 g of xanthan and 0.5 g of hydroxypropylmethylcellulose 15 cps are added, and the mixture is stirred until uniform swelling is achieved. Flavors are also added if desired.

Example C 0.1 g of cyclamate sodium and 0.15 g of sodium benzoate are successively added to and dissolved in 100 ml of purified water. 3.0 g of crospovidone are then dispersed with a stirrer in the solution obtained in this way. 6.0 g of a preparation obtained as in Example 6 are stirred into the dispersion. 1.5 g of hydroxypropylmethylcellulose 15 cps are added, and the mixture is stirred until uniform swelling is reached. Flavors are also added if desired.

Example D 0.1 g of cyclamate sodium and 0.2 g of sorbic acid are successively added to and dissolved in 100 ml of purified water. 3.0 g of crospovidone are then dispersed with a stirrer in the solution obtained in this way. 4.0 g of a preparation obtained as in Example 2 are stirred into the dispersion. 2.0 g of hydroxypropylmethylcellulose 15 cps are added, and the mixture is stirred until uniform swelling is reached. Flavors are also added if desired.

Example E 0.1 g of cyclamate sodium and 0.15 g of sorbic acid are successively added to and dissolved in 100 ml of purified water. 2.0 g of microcrystalline cellulose are then dispersed with a stirrer in the solution obtained in this way. 8.0 g of a preparation obtained as in Example 9 are stirred into the dispersion. 2.0 g of Polyvidone 30 are added, and the mixture is stirred until uniform swelling is reached. Flavors are also added if desired.

The invention claimed is:

1. A pharmaceutical preparation in juice (suspension) form with a viscosity of less than 500 mPa.s (determined with a rotational viscometer) for oral administration of an acid-labile active ingredient where a plurality of individual active ingredient units are dispersed in a thickened base composed of one or more pharmaceutical excipients, wherein the individual active ingredient units are microspheres and wherein the acid-labile active compound is selected from the group consisting of an acid-labile proton pump inhibitor, a salt of an acid-labile proton pump inhibitor with a base and a hydrate of a salt of an acid-labile proton pump inhibitor with a base and is present in the individual active ingredient units in a matrix composed of a mixture comprising at least one solid paraffin and one or more substances selected from the group consisting of a fatty alcohol, a triglyceride and a fatty acid ester, and where the thickened base is aqueous, and at least one thickener selected from the group consisting of substituted celluloses, polyvinylpyrrolidone [polyvidone types], sheet silicates, alginates, alginic acids and mixtures thereof is present as excipient.

2. A pharmaceutical preparation in juice (suspension) form for oral administration according to claim 1, where the acid-labile active ingredient is present in the individual active ingredient units i) in a matrix composed of a mixture comprising at least one fatty alcohol and at least one solid paraffin, ii) in a matrix composed of a mixture comprising at least one triglyceride and at least one solid paraffin or iii) in a matrix composed of a mixture comprising, at least one fatty acid ester and at least one solid paraffin.

3. A pharmaceutical preparation as claimed in claim 1, which is a suspension ready for use.

4. A pharmaceutical preparation as claimed in claim 1, where the proportion of thickener based on the preparation ready for use is from 0.1 to 10% by weight.

5. A pharmaceutical preparation as claimed in claim 1, where an excipient selected from the group consisting of flavors, flavoring substances, buffer substances, preservatives and emulsifiers is additionally present in the thickened base.

6. A pharmaceutical preparation as claimed in claim 1, wherein pantoprazole, a salt of pantoprazole, a solvate of pantoprazole or a salt thereof is present as acid-labile proton pump inhibitor.

7. A dosage form for oral administration of an acid-labile active ingredient, comprising a preparation as claimed in claim 1, where the preparation is present in a container suitable for oral administration.

8. A preparation according to claim 1, wherein the proton pump inhibitor is pantoprazole sodium sesquihydrate, (−)-pantoprazole sodium sesquihydrate, pantoprazole magnesium dihydrate, omeprazole magnesium, omeprazole or esomeprazole magnesium.

9. A preparation according to claim 1, wherein the microspheres are monomodal microspheres and have a particle size range of 50-400 μm.

10. A preparation according to claim 1, wherein, in the mixture, one or more further excipients, selected from the group consisting of polymers, sterols and basic compounds, is/are present in the matrix of the individual active compound units.

11. A preparation according to claim 10, wherein the polymer is selected from the group consisting of povidone, vinylpyrrolidone/vinyl acetate copolymer, polyvinyl acetate, cellulose ethers, cellulose esters, methacrylic acid/methyl methacrylate copolymer, methacrylic acid/ethyl methacrylate copolymer and mixtures thereof.

12. A preparation according to claim 10, wherein the sterol is selected from the group consisting of ergosterol, stigmasterol, sitosterol, brassicasterol, campesterol, cholesterol, lanosterol and mixtures thereof.

13. A preparation according to claim 10, wherein the basic compound is selected from the group consisting of an inorganic basic salt, a salt of a fatty acid, an amine and a fatty amine.

14. The preparation according to claim 13, wherein the inorganic basic salt is selected from the group consisting of ammonium carbonate and sodium carbonate.

15. The preparation according to claim 13, wherein the salt of a fatty acid is sodium stearate.

16. The preparation according to claim 13, wherein the amine is selected from the group consisting of meglumine, diethylamine, triethylamine and TRIS (2-amino-2-hydroxymethyl-1,3-propandiol).

17. The preparation according to claim 13, wherein the fatty amine is stearylamine.

18. The preparation according to claim 1, wherein the fatty alcohol is selected from the group consisting of cetyl alcohol, myristyl alcohol, lauryl alcohol, stearyl alcohol and mixtures thereof.

19. A preparation according to claim 1, wherein the triglyceride is selected form the group consisting of tristearate, tripalmitate, trimyristate and mixtures thereof.

20. A preparation according to claim 1, wherein the fatty acid ester is cetyl palmitate.

21. A preparation according to claim 1, wherein the solid paraffin is paraffinum solidum or ozocerite.

22. A method of treating a gastric disorder in a patient comprising administering to a patient in need thereof a pharmaceutical preparation according to claim 1.

23. A process for manufacturing a pharmaceutical preparation according to claim 1, comprising introducing individual active ingredient units into a dispersion of the thickener in water or by introducing the thickener into a dispersion of the individual active ingredient units in water.

* * * * *